United States Patent [19]

Rathgeb et al.

[11] 3,936,293
[45] Feb. 3, 1976

[54] METHOD OF SELECTIVE WEED CONTROL WITH CERTAIN CHLOROACETAMIDES

[75] Inventors: Paul Rathgeb, Basel, Switzerland; Jean Claude Tournayre, Lunel, France; Christian Vogel, Binningen, Switzerland

[73] Assignee: Ciba-Geigy Corporation, Ardsley, N.Y.

[22] Filed: Jan. 20, 1975

[21] Appl. No.: 542,531

Related U.S. Application Data

[62] Division of Ser. No. 331,168, Feb. 9, 1973, Pat. No. 3,875,228.

[30] Foreign Application Priority Data

Feb. 11, 1972 Switzerland.......................... 2034/72

[52] U.S. Cl. ................................................. 71/118
[51] Int. Cl.² ............................................. A01N 9/20
[58] Field of Search ......................................... 71/118

[56] References Cited
UNITED STATES PATENTS

| | | | |
|---|---|---|---|
| 3,255,247 | 6/1966 | Olin .................................. | 260/562 |
| 3,691,234 | 9/1972 | Kiefer et al............................ | 71/118 |

FOREIGN PATENTS OR APPLICATIONS

| | | | |
|---|---|---|---|
| 1,170,654 | 11/1969 | United Kingdom................... | 71/118 |
| 923,128 | 4/1963 | United Kingdom................... | 71/118 |

OTHER PUBLICATIONS

Takahashi et al., "Syntheses of Analgesics," (1962) CA59, p. 611 (1963).
Takahashi et al., II "1-Indanamines," (1966) CA65, p. 668 (1966).
Yamazoe et al., "Experimental Chemotherapy etc.," (1968) CA70, No. 87366r (1969).
Hach, "Local Anesthetics II; Further Analogs, etc.," (1953) Ca49, p. 979 (1954).

*Primary Examiner*—Glennon H. Hollrah
*Attorney, Agent, or Firm*—Harry Falber

[57] ABSTRACT

Agent for the regulation of plant growth, which agent contains as active substance at least one acylamine of the formula

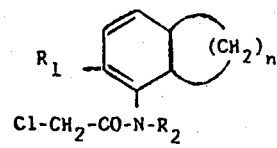

wherein $R_1$ represents hydrogen, methyl or ethyl, $R_2$ represents hydrogen, methyl, ethyl, n-propyl, isopropyl, methoxyethyl, allyloxymethyl or lower alkyloxymethyl, and $n$ denotes the number 3 or 4.

7 Claims, No Drawings

METHOD OF SELECTIVE WEED CONTROL WITH CERTAIN CHLOROACETAMIDES

This is a division of application Ser. No. 331,168, filed on Feb. 9, 1973 now U.S. Pat. No. 3,875,228.

The present invention relates to acylamines of bicyclic hydrocarbons, to processes for their production, also to plant-regulating agents containing these compounds as active substances, as well as to processes for plant regulation, particularly for the control of weeds by application of the new active substances or of agents containing them.

The new acylamines correspond to formula I

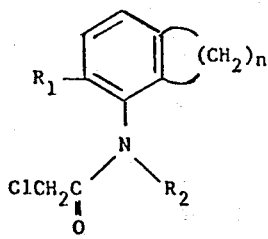

wherein
$R_1$ represents hydrogen, methyl or ethyl,
$R_2$ represents hydrogen, methyl, ethyl, n-propyl, isopropyl, methoxyethyl, allyloxymethyl or lower alkyloxymethyl, and
n represents the number 3 or 4.

The new active substances of the present invention are acylated 5-amino-tetralins and acylated 4-aminoindanes.

The lower alkyl radical in the lower alkyloxymethyl group can be: methyl, ethyl, n-propyl, isopropyl, n-butyl, isobutyl, sec.butyl or tert.butyl.

Preferred active substances are those compounds of formula I wherein n = 3.

Of these compounds, particularly valuable ones are compounds in which $R_1$ represents methyl or ethyl, and $R_2$ represents a methoxymethyl, ethoxymethyl or isopropoxymethyl group.

The compounds of formula I are obtained according to the present invention by a process in which an amine of formula II

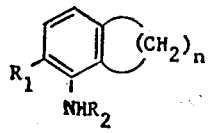

is reacted with a compound suitable for halogenoacetylation, preferably with a chloroacetanhydride or a chloroacetyl halide. In formula II, the symbols $R_1$, $R_2$ and n have the meanings given under formula I.

The reactions can be performed in the presence or absence of solvents or diluents inert to the reactants. The following are, for example, suitable: aliphatic, aromatic or halogenated hydrocarbons such as benzene, toluene, xylenes, petroleum ether, chlorobenzene, methylene chloride, ethylene chloride, chloroform; ethers and ethereal compounds such as dialkyl ether, dioxane, tetrahydrofuran; nitriles such as acetonitriles; N,N-dialkylated amides such as dimethylformamide; also dimethylsulphoxide as well as mixtures of these solvents with each other.

Chloroacetylation can also be performed with chloroacetic acid, its esters or amides. The reaction temperatures are between 0° and 200°, preferably between 20° and 100°C. In some cases the chloroacetylation is carried out in the presence of an acid-binding agent. Suitable acid binding agents for this purpose are tertiary amines such as trialkylamines, e.g. triethylamine, pyridine and pyridine bases, or inorganic bases such as the oxides and hydroxides, hydrogen carbonates and carbonates of alkali metals and alkaline-earth metals. The acid binding agent may also be the respective amine of formula II, which in this case has to be used in excess.

Compounds of formula I wherein $R_2$ represents an allyloxymethyl group or lower alkyloxymethyl group can be produced by a process in which an amide of formula III

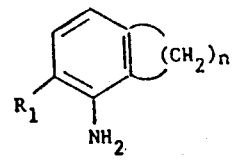

is converted in a manner known per se with formaldehyde into the corresponding azomethine of formula IV

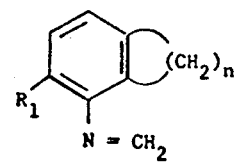

this then reacted with a halogenoacetyl chloride of formula V

Hal - CO CH$_2$Cl (V), and subsequently with an alkanol of formula VI
$R_3$ - OH
in the presence of an acid-binding agent.

In formulae III and IV, the symbols $R_1$ and n have the meanings given under formula I. Hal in formula V stands for halogen, preferably for chlorine or bromine, while $R_3$ in formula VI represents the lower alkyl group or the allyl group.

The individual reaction steps of this second process are performed in the presence of solvents or diluents inert to the reactants, such as are given above, with the absence of moisture. A chloroacetamide is obtained as the intermediate, which can be reacted, after the solvent has been distilled off, direct with the alkanol of formula VI. This step of the process is performed in the presence of an acid-binding agent; suitable acid-binding agents in this case are: inorganic and organic bases such as, e.g. alkali metal and alkaline-earth metal hydroxides and -carbonates; trialkylamines such as trimethylamine, triethylamine, dialkylanilines, pyridine and pyridine bases; alkali alkanolates of lower alkanols such as sodium methylate, sodium ethylate, potassium ethylate, etc. The reaction temperatures are between −20° and 110°C.

In the performance of this second process it is advisable not to isolate either the azomethines given as intermediates of formula IV, or the compounds obtained therefrom with halogenoacetyl chloride, but to use them as crude products in the form of solutions in the further reactions.

In the case of the starting materials of formula III, these are 4-amino-indanes and 5-amino-tetralins, of which only certain ones have been hitherto described in the literature.

4-Amino-5-ethylindanes according to formula III which have not been hitherto described are obtained by processes known per se by reaction of 4-amino-indane with ethylene in the presence of aluminium powder and aluminium chloride (Friedel-Crafts reaction).

5-Methyl-4-amino-indane is obtained from indane by chloromethylation, subsequent hydrogenating dehalogenation, nitration and reduction of the nitro group. 5-Aminotetralins (= 5-amino-1,2,3,4-tetrahydronaphthalenes) are obtained by catalytic hydrogenation of the corresponding 6-alkyl-α-naphthylamines [cp. Schroeter, Ann. 426, from p. 1, (1922)].

The following examples illustrate the process according to the invention. Further compounds of formula I which have been produced by the described processes are listed in the following table. The temperatures are expressed in degrees Centigrade.

EXAMPLE 1 a. An amount of 40 g of 4-amino-indane is mixed with 40 ml of isopropylbromide, and the mixture heated for 5 hours in a sealed tube at 130° – 140°. After cooling of the reaction mixture, diluted ammonia is added until an alkaline reaction is obtained, and extraction then performed with diethyl ether. The organic phases are concentrated by evaporation and the residue distilled in high vacuum. There is thus obtained 47 g of 4-isopropylamino-indane (B.P. 95°/1 Torr; $n_D^{20}$ = 1.5533).

b. An amount of 34 g of chloroacetic acid anhydride is added to 29 g of 4-isopropylamino-indane; the reaction temperature rises in the process to 50°. The homogeneous mixture is heated for one hour on a boiling water-bath; the mixture is then cooled to 35° – 40°, an addition made of 150 ml of diethyl ether, and the whole cooled to 0°. There thus crystallises 29 g of N-chloroacetyl-N-isopropyl-4-amino-indane, M.P. 59° to 61° (compound No. 1).

EXAMPLE 2 a. 5-Amino-1,2,3,4-tetrahydronaphthalene is obtained by hydrogenation of α-naphthylamine with Raney-nickel at 15 atm. and at a temperature of 180° [anolog. to Schroeter, Ann. 426, p. 1 (1922)]. The boiling point is at 92°/0.7 Torr; $n_D^{20}$ = 1.5910.

b. An ethereal solution of 90 g of chloroacetic acid anhydride is added dropwise to 73.6 g of 5-amino-1,2,3,4-tetrahydronapthalene in 1000 ml of diethyl ether. The temperature should not exceed 30°. The mixture is stirred for a further half hour at room temperature, then cooled to 0° and the precipitated product filtered off. After recrystallisation from ethanol, there is obtained 100 g of 5-chloroacetamino-1,2,3,4-tetrahydronaphthalene having a melting point of 155° – 157° (compound No. 2).

EXAMPLE 3 a. A mixture of 106 g (0.8 mole) of 4-amino-indane, 4 g of aluminium chloride and 1.6 g of aluminium shot is heated in an autoclave to 300°C. After injection of ethylene at 200 bar, the reaction mixture is maintained for one hour at 300°C. By distillation of the green-black crude product in high vacuum there is obtained 106.9 g of 5-ethyl-4-amino-indane, B.P. 72 to 74°C/0.001 Torr.

b. An amount of 1 ml of 25 percent methanolic trimethylamine solution is added to the solution of 53 g (0.33 mole) of 5-ethyl-4-amino-indane and 12 g (0.4 mole) of paraformaldehyde in 250 ml of benzene, and the whole refluxed for 5 hours under a water separator. The slightly yellow solution is concentrated by evaporation and in the crude condition further processed.

c. The solution of 17.3 g (0.1 mole) of the azomethine obtained according to b) in 20 ml of absolute benzene is added dropwise in the course of 20 minutes at −3° to 0°C to a solution of 11.3 g (0.1 mole) of chloroacetyl chloride in 40 ml of absolute benzene, and the temperature of the reaction mixture thereupon raised within 30 minutes to 25°C. After the addition of 60 ml of absolute methanol, the temperature is increased to 60°C; an addition is made dropwise to the solution within 20 minutes of 11.3 g (0.11 mole) of triethylamine, and the whole finally stirred for 1 hour at 60°C. After concentration of the reaction solution in vacuo, the crystalline residue is taken up in 300 ml of diethyl ether, the ether solution repeatedly washed with water, dried and concentrated by evaporation. By dissolving of the distillation residue in petroleum ether, and crystallising at −30° to −40°C, there is obtained N-methoxy-methyl-N-chloroacetyl-5-ethyl-4-amino-indane (compound No. 3) as colourless crystals, M.P. 57° to 60°C.

All together there are produced the following compounds of formula I:

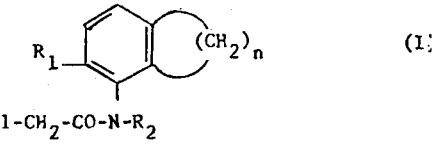

$$Cl-CH_2-CO-N-R_2$$

| Comp. No. | $R_1$ | $R_2$ | n | Physical data |
|---|---|---|---|---|
| 1 | H | isoC$_3$H$_7$ | 3 | M.P. 59 – 61° |
| 2 | H | H | 4 | M.P. 155 – 157° |
| 3 | C$_2$H$_5$ | —CH$_2$—O—CH$_3$ | 3 | M.P. 57 – 60° |
| 4 | C$_2$H$_5$ | —CH$_2$—O—isoC$_3$H$_7$ | 3 | $n_D^{20}$ 1.5350 |
| 5 | C$_2$H$_5$ | —CH$_2$—O—C$_2$H$_5$ | 3 | M.P. 42 – 45° |
| 6 | H | —CH$_2$—O—CH$_3$ | 3 | M.P. 52 – 54° |
| 7 | CH$_3$ | —CH$_2$—O—CH$_3$ | 4 | M.P. 56 – 58° |
| 8 | C$_2$H$_5$ | —CH$_2$—O—CH$_3$ | 4 | viscous oil |
| 9 | CH$_3$ | H | 4 | M.P. 59 – 61° |
| 10 | H | H | 3 | M.P. 128 – 131° |
| 11 | H | isoC$_3$H$_7$ | 4 | M.P. 61 – 63° |
| 12 | H | n-C$_3$H$_7$ | 4 | M.P. 71 – 73° |
| 13 | H | C$_2$H$_5$ | 4 | M.P. 51 – 52° |
| 14 | H | n—C$_3$H$_7$ | 3 | M.P. 41 – 42° |
| 15 | H | CH$_3$ | 3 | M.P. 60 – 61° |
| 16 | H | CH$_3$ | 4 | M.P. 106 – 107° |
| 17 | H | —CH$_2$—CH$_2$—O—CH$_3$ | 3 | M.P. 57 – 59° |
| 18 | H | —CH$_2$—CH$_2$—O—CH$_3$ | 4 | M.P. 41 – 42° |
| 19 | H | —CH$_2$—O—CH$_2$—CH—CH$_2$ | 3 | $n_D^{20}$ 1.5479 |
| 20 | H | —CH$_2$'O—C$_2$H$_5$ | 3 | $n_D^{20}$ 1.5494 |
| 21 | H | —CH$_2$—O—nC$_3$H$_7$ | 3 | $n_D^{20}$ 1.5396 |
| 22 | H | —CH$_2$—O—tert.C$_4$H$_9$ | 3 | $n_D^{20}$ 1.5310 |
| 23 | H | —CH$_2$—O—isoC$_3$H$_7$ | 3 | $n_D^{20}$ 1.5411 |
| 24 | H | —CH$_2$—O—nC$_4$H$_9$ | 3 | $n_D^{20}$ 1.5381 |
| 25 | H | —CH$_2$—O—Sec.C$_4$H$_9$ | 3 | $n_D^{20}$ 1.5340 |
| 26 | H | —CH$_2$—O—isoC$_4$H$_9$ | 3 | $n_D^{20}$ 1.5329 |
| 27 | C$_2$H$_5$ | —CH$_2$—O—CH$_3$ | 4 | highly viscous oil |

One of the problems at present associated with weed control is that of effecting the construction of difficulty controllable perennial grasses known biologically under the collective term of 'millet-related' plants. Belonging to these are species such as *Setaria*, *Digitaria* and *Echinochloa*. It has now been shown that the compounds of formula I effectively and lastingly destroy precisely these weeds that are known to be extremely resistant, and simultaneously control also other species of grasses such as *Cyperaceae* (e.g. *Cyperus esculentus*), or such as the *Lolium* and *Alopecurus* species.

Useful-plant crops, such as maize, cereals, soya bean, lucerne, peas, beans, potatoes, cotton, brassica (rape and cabbage), sugar beet, sugar cane, sunflower or rice, are not damaged. The compounds of formula I therefore have a very wide practical field of application.

To be particularly emphasised is the use of the said compounds for the control of grass (*Echinochloa sp.*) in upland rice crops and in paddy rice crops. Since the active substances in the normally applied concentrations are not toxic and do not impair the biological equilibrium, they are particularly suitable for application in paddy rice crops. They can also be used for the control of weeds in border areas, such as in ditches, canal beds and on embankments, etc.

The active substances are applied before (pre-emergence) or after (post-emergence) emergence of the plants, preferably before. The applied amounts are between 0.1 and 10 kg per hectare; however, excellent control or destruction of weeds is effected even with applied amounts of 0.5 kg per hectare. In order to prevent weed infestation, e.g. of railway embankments, factory sites, streets, etc., the amounts applied are usually up to 10 kg or more per hectare.

Furthermore, the active substances of formula I also possess growth-regulating properties in that, in the case of grasses (e.g. on existing cultivated lawns), they retard growth height and increase tillering. Weeds that intensively and rapidly run to seed are inhibited in germination and sprouting, and thus removed from crops of useful plants. The present acylated amines of formula I possess moreover defoliating properties, and can be used for the retarding of blossom. The capacity of plants to store plant constituents is, as a rule, improved by the present active substances. Thus, for example, the sugar content in sugar beet and sugar cane is increased, and likewise the starch content in potatoes, or the fat content in soya beans or in groundnuts.

1. Herbicidal action with application of the active substances before emergence of the plants Immediately after the sowing of the test plants in seed trays, the active substances are applied as an aqueous dispersion (obtained from a 25 percent wettable powder) to the surface of the soil. The seed trays are then maintained at 22° – 25° with 50 – 70 percent relative humidity. The results of the test are evaluated after 28 days. These results are given in Table I.

Evaluation is on the basis of the following scale of values:

9 = plants undamaged (as in control test)
1 = plants dead
8–2 = intermediate stages of damage
— = not tested Table 1

| Compound No. | Applied amount in kg of active subst./hectare | Amaranthus | Echinochloa | Setarin | Digitaria | Poa | Cyperus | Alopecurus | Lolium | maize | cotton | soya bean | wheat | sugar beet |
|---|---|---|---|---|---|---|---|---|---|---|---|---|---|---|
| 7 | 4 | — | 1 | 1 | 1 | 1 | 1 | 1 | 1 | 7 | 9 | 8 | 8 | 8 |
|   | 2 | — | 1 | 1 | 1 | 2 | 1 | 2 | 2 | 7 | 9 | 8 | 8 | 9 |
|   | 1 | — | 2 | 2 | 2 | 2 | 2 | 4 | 2 | 8 | 9 | 9 | 9 | 9 |
|   | 0.5 | — | 2 | 2 | 3 | 3 | 3 | — | 3 | 9 | 9 | 9 | 9 | 9 |
| 15 | 4 | — | 1 | 1 | 1 | — | 1 | — | 1 | 9 | 9 | — | 8 | 9 |
|   | 2 | — | 1 | 2 | 1 | — | 1 | — | 1 | 9 | 9 | — | 9 | 9 |
|   | 1 | — | 1 | 2 | 2 | — | 2 | — | 2 | 9 | 9 | — | 9 | 9 |
|   | 0.5 | — | 2 | 4 | — | — | 3 | — | 2 | 9 | 9 | — | 9 | 9 |
| 3 | 4 | 1 | 1 | 1 | 1 | 1 | — | 1 | 1 | — | 9 | 7 | — | — |
|   | 2 | 1 | 1 | 1 | 1 | 1 | — | 2 | 1 | 7 | 9 | 7 | — | — |
|   | 1 | 1 | 1 | 1 | 1 | 1 | — | 2 | 2 | 8 | 9 | 8 | — | — |
|   | 0.5 | 1 | 1 | 2 | 1 | 3 | — | 2 | 2 | 9 | 9 | 9 | — | — |
| 4 | 4 | 1 | 1 | 1 | 1 | 1 | — | 1 | 1 | 8 | 8 | 8 | — | — |
|   | 2 | 1 | 1 | 1 | 1 | 1 | — | 1 | 1 | 8 | 9 | 9 | 8 | — |
|   | 1 | 1 | 1 | 1 | 1 | 1 | — | 2 | 2 | 9 | 9 | 9 | 8 | — |
|   | 0.5 | 2 | 1 | 2 | 4 | 1 | — | 2 | 2 | 9 | 9 | 9 | 9 | — |
| 5 | 4 | 1 | 1 | 1 | 1 | 1 | — | 1 | 1 | 8 | — | 7 | — | — |
|   | 2 | 1 | 1 | 1 | 1 | 1 | — | 2 | 2 | 8 | 9 | 7 | — | 7 |
|   | 1 | 1 | 1 | 1 | 1 | 1 | — | 2 | 2 | 9 | 9 | 8 | — | 8 |
|   | 0.5 | 1 | 1 | 1 | 1 | 2 | — | 2 | 2 | 9 | 9 | 9 | — | 8 |
| 20 | 4 | 1 | 1 | 1 | 1 | — | — | 2 | — | 9 | 9 | 9 | 7 | 8 |
|   | 2 | 1 | 1 | 2 | 2 | — | — | 2 | — | 9 | 9 | 9 | 8 | 8 |
|   | 1 | 1 | 2 | 2 | 2 | — | — | 3 | — | 9 | 9 | 9 | 9 | 9 |
|   | 0.5 | 2 | 2 | 3 | 2 | — | — | — | — | 9 | 9 | 9 | 9 | 9 |
| 23 | 4 | 1 | 1 | 1 | 1 | — | 1 | — | — | 9 | 8 | 9 | 9* | 9 |
|   | 2 | 1 | 2 | 2 | 2 | — | 1 | — | — | 9 | 9 | 9 | 9* | 9 |
|   | 1 | 1 | 2 | 2 | 3 | — | 1 | — | — | 9 | 9 | 9 | 9* | 9 |
|   | 0.5 | 1 | 2 | 3 | 4 | — | 2 | — | — | 9 | 9 | 9 | 9* | 9 |
| 1 | 4 | — | 1 | 1 | 1 | 1 | 1 | — | 1 | 9 | 9 | 9 | 9 | 9 |
|   | 2 | — | 1 | 1 | 1 | 2 | 1 | — | 1 | 9 | 9 | 9 | 9 | 9 |
|   | 1 | — | 1 | 1 | 3 | 2 | 1 | — | 1 | 9 | 9 | 9 | 9 | 9 |

Table 1-continued

| Compound No. | Applied amount in kg of active subst./hectare | Ama-ranthus | Echino-chloa | Setarin | Digitaria | Poa | Cyperus | Alope-curus | Lolium | maize | cotton | soya bean | wheat | sugar beet |
|---|---|---|---|---|---|---|---|---|---|---|---|---|---|---|
| | 0.5 | — | 2 | 2 | 3 | 2 | 2 | — | 2 | 9 | 9 | 9 | 9 | 9 |

*Evaluation for barley instead of wheat

2. CONTROL OF WEEDS IN RICE

Rice (Oryza oryzoides) is sown in garden soil contained in clay dishes, and in a similar manner likewise weeds. The active-substance solution, prepared from a 25 percent wettable powder, is applied to the surface of the soil immediately after sowing. The dishes are kept in a greenhouse at 24°–27° with 70 percent relative humidity. An evaluation of the test results is made after 28 days based on the scale of values used in the previous example.

| Compound No | Applied amount in kg AS/hect. | Setaria itolica | Echinochloa crus galli | Rice |
|---|---|---|---|---|
| 6 | 4 | — | 1 | 9 |
|   | 2 | — | 1 | 9 |
|   | 1 | — | 2 | 9 |
| 20 | 4 | 1 | 1 | 7 |
|    | 2 | 1 | 1 | 8 |
|    | 1 | 2 | 2 | 9 |
| 21 | 4 | 2 | 1 | 7 |
|    | 2 | 2 | 1 | 8 |
|    | 1 | 2 | 2 | 9 |
| 24 | 4 | 1 | 1 | 9 |
|    | 2 | 2 | 1 | 9 |
|    | 1 | 3 | 1 | 9 |
| 25 | 4 | 1 | 1 | 8 |
|    | 2 | 2 | 1 | 9 |
|    | 1 | 3 | 1 | 9 |
| 19 | 4 | 1 | 1 | — |
|    | 2 | 2 | 1 | 9 |
|    | 1 | 3 | 1 | 9 |
| 15 | 4 | 1 | 1 | 7 |
|    | 2 | 2 | 1 | 9 |
|    | 1 | 2 | 1 | 9 |

In the production of herbicidal agents, the active substances are mixed with suitable carriers and/or distributing agents. For the widening of the sphere of action of these agents, it is possible to add to them other herbicides, for example, of the series of triazines such as halogen-diamino-s-triazines, alkoxy- and alkylthio-diamino-s-triazines, triazoles, diazines such as uracils, aliphatic carboxylic acids and halogencarboxylic acids, halogenated benzoic acids and phenylacetic acids, aryloxyalkanecarboxylic acids, hydrazides, amides, nitriles, esters of such carboxylic acids, carbamic acid and thiocarbamic acid esters, and phenylureas.

Herbicidal agents according to the invention are produced in a manner known per se by the intimate mixing and grinding of active substances of the general formula I with suitable carriers, optionally with the addition of dispersing agents or solvents which are inert to the active substances. The active substances can be obtained and used in the following forms:

solid preparations: dusts, scattering agents, granulates, (coated granulates, impregnated granulates and homogeneous granulates);

water-dispersible concentrates of the active substance: wettable powders, pastes, emulsions;

liquid preparations: solutions.

The solid preparations (dusts, scattering agents, granulates) are produced by the mixing of the active substances with solid carriers. Suitable carriers are, e.g. kaolin, talcum, bole, loess, chalk, limestone, ground limestone, Attaclay, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

The particle size of the carriers is for dusts advantageously up to about 0.1 mm; for scattering agents from about 0.075 mm to 0.2 mm; and for granulates 0.2 mm or coarser.

The concentrations of active substance in the solid preparation forms are from 0.5 to 80 percent.

To these mixtures may also be added additives stabilising the active substance, and/or non-ionic, anion-active, and cation-active substances, which, for example, improve the adhesiveness of the active substances on plants and on parts of plants (adhesives and agglutinants), and/or ensure a better wettability (wetting agents) and dispersibility (dispersing agents). Suitable adhesives are, for example, the following: olein/chalk mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, its alkali metal and alkaline-earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide, propylene oxide, polyvinyl pyrrolidones, polyvinyl alcohols, condensation products of urea and formaldehyde, as well as latex products.

Water-dispersible concentrates of active substance, i.e., wettable powders, pastes and emulsion concentrations, are agents which can be diluted with water to obtain any desired concentration. They consist of active substance, carrier, optionally additives which stabilise the active substance, surface-active substances, and anti-foam agents and, optionally, solvents. The concentration of active substance in these agents is 5 to 80 percent.

The wettable powders and the pastes are obtained by the mixing and grinding of the active substances with dispersing agents and pulverulent carriers, in suitable devices, until homogeneity is attained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylaryl sulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, ditertiary acetylene glycols, dialkyl dilauryl ammonium chloride, and fatty acid alkali-metal and alkaline-earth metal salts.

Suitable anti-foam agents are, for example, silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. Dispersing agents such as those mentioned in the preceding paragraphs, organic solvents and water are used in the preparation of emulsion concentrates and pastes. Suitable solvents are, e.g. the following: alcohols, benzene, xylenes, toluene, dimethylsulphoxide, N,N-dialkylated amides, N-oxides of amines, especially trialkylamines, and mineral oil fractions boiling in the range of 120° to 350°. The solvents must be practically odourless, non-phytotoxic, inert to the active substances, and not readily inflammable.

Furthermore, the agents according to the invention can be used in the form of solutions. For this purpose the active substance (or several active substances) of the general formula I is (or are) dissolved in suitable organic solvents, mixtures of solvents, water, or mixtures of organic solvents with water. As organic solvents it is possible to use aliphatic and aromatic hydrocarbons, their chlorinated derivatives, alkylnaphthalenes, mineral oils on their own or in admixture with each other. The solutions should contain the active substances in a concentration of from 1 to 20 percent. These solutions can be applied either with the aid of a propellent gas (as a spray), or with special spraying devices (such as aerosol).

Other biocidal active substances or agents may be added to the described agents according to the invention. For the widening of their sphere of action, the new agents may also contain, in addition to the stated compounds of the general formula I, e.g. insecticides, fungicides, bactericides, fungistatics, bacteriostatics or nematocides. The agents according to the invention can also contain fertilisers, trace elements, etc.

Preparations of the new active substances of the general formula I are described in the following. The term 'parts' denotes parts by weight.

GRANULATE

The following substances are used to produce a 5 percent granulate:
5 parts of active substance No. 1,
0.25 parts of epichlorohydrin,
0.25 parts of cetyl polygylcol ether,
3.50 parts of polyethylene glycol,
91 parts of kaolin (particle size 0.3 to 0.8 mm).

The active substance is mixed with epichlorohydrin and the mixture dissolved in 6 parts of acetone; the polyethylene glycol and cetyl polyglycol ether are then added. The thus obtained solution is sprayed on kaolin and the acetone subsequently evaporated off in vacuo.

WETTABLE POWDER

The following constituents are used for the preparation of a) a 50 percent, b) a 25 percent and c) a 10 percent wettable powder:

a) 50 parts of active substance No. 2,
5 parts of sodium dibutyl naphthylsulphonate,
3 parts of naphthalenesulphonic acid phenolsulphonic acid/formaldehyde condensate 3:2:1,
20 parts of kaolin,
22 parts of Champagne chalk;
b) 25 parts of active substance No. 1,
5 parts of the sodium salt of oleyl methyl tauride,
2.5 parts of naphthalenesulphonic acid/formaldehyde condensate,
0.5 parts of carboxymethylcellulose,
5 parts of neutral potassium aluminium silicate,
62 parts of kaolin;
c) 10 parts of active substance No. 3,
3 parts of a mixture of the sodium salts of saturated fatty alcohol sulphates,
5 parts of naphthalenesulphonic acid/formaldehyde condensate,
82 parts of kaolin.

The given active substance is absorbed onto the appropriate carriers (kaolin and chalk) and the whole subsequently mixed and ground. Wettable powders are obtained having excellent wettability and suspension properties. It is possible to prepare from such wettable powders, by dilution with water, suspensions of any desired concentration of active substance. These suspensions are employed for the control of weeds and wild grasses in cultivated crops.

PASTE

The following substances are used for the preparation of a 45 % paste:
45 parts of active substance No. 19 or No. 2,
5 parts of sodium aluminium silicate,
14 parts of cetyl polyglycol ether having 8 moles of ethylene oxide,
1 part of oleyl polyglycol ether having 5 moles of ethylene oxide,
2 parts of spindle oil,
10 parts of polyethylene glycol,
23 parts of water.

The active substance is intimately mixed and ground, in suitable apparatus, with the additives. A paste is obtained from which can be prepared, by dilution with water, suspensions of any desired concentration.

EMULSION CONCENTRATE

The following substances are mixed together in the preparation of a 25 percent emulsion concentrate:
25 parts of active substance No. 2,
5 parts of a mixture of nonyl phenol polyoxyethylene and calcium dodecylbenzene sulphonate,
35 parts of 3,5,5-trimethyl-2-cyclohexen-1-one,
35 parts of dimethylformamide.

This concentrate can be diluted with water to obtain emulsions of suitable concentration. Such emulsions are suitable for the control of weeds in cultivated crops.

We claim:
1. Process for the selective control of undesired plant growth in useful plant crops which comprises applying to the plant area a growth controlling effective amount of an active substance corresponding to the formula

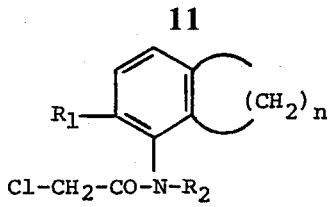

wherein R₁ represents hydrogen, methyl or ethyl; R₂ represents hydrogen, methyl, ethyl, n-propyl, isopropyl, methoxyethyl, allyloxymethyl or lower alkyloxymethyl; and n denotes the number 3 or 4.

2. The process of claim 1, wherein n=3 in said active substance.

3. The process of claim 2, wherein in said active substance R₁ represents methyl or ethyl, and R₂ represents methoxymethyl, ethoxymethyl or isopropoxymethyl.

4. The process of claim 2, wherein said active substance is N-ethoxymethyl-N-chloroaceto-4-amino-5-ethyl-indane.

5. The process of claim 2, wherein said active substance is N-isopropoxymethyl-N-chloroaceto-4-amino-5-ethyl-indane.

6. The process of claim 2, wherein said active substance is N-methoxymethyl-N-chloroaceto-4-amino-5-ethyl-indane.

7. The process of claim 2, wherein said active substance is N-isopropyl-N-chloroaceto-4-amino-indane.

* * * * *